United States Patent [19]

Strickland et al.

[11] Patent Number: 4,493,476
[45] Date of Patent: Jan. 15, 1985

[54] SLIDE VALVE FOR CONTROLLING FLUID FLOW

[76] Inventors: Reid A. Strickland; Timothy J. Roller, both of 689 Ogden Parma Town Line Rd, Spencerport, N.Y. 14559

[21] Appl. No.: 425,897

[22] Filed: Sep. 28, 1982

[51] Int. Cl.³ .................. F16K 11/06; F16K 3/314
[52] U.S. Cl. ................................ 251/176; 251/195; 251/327; 251/368; 137/625.18; 137/625.48
[58] Field of Search ............ 251/326, 327, 193, 195; 137/625.18, 625.48; 251/176, 368

[56] References Cited

U.S. PATENT DOCUMENTS

| | | | |
|---|---|---|---|
| 3,035,809 | 5/1962 | Dickinson | 251/192 |
| 3,150,517 | 9/1964 | Kuffer et al. | 137/625.18 X |
| 3,294,119 | 12/1966 | Hunt | 251/176 X |
| 3,521,674 | 7/1970 | Dodson et al. | 251/176 X |
| 4,334,552 | 6/1982 | Blanchard | 251/176 X |

Primary Examiner—Arnold Rosenthal
Attorney, Agent, or Firm—Stonebraker, Shepard & Stephens

[57] ABSTRACT

A slide valve for controlling fluid flow, useful especially but not exclusively where high precision and high quality performance are required, as in scientific or medical apparatus and equipment. A valve body, preferably of plastic material, has a channel for receiving a valve slide assembly, the channel providing two surfaces parallel to and spaced from each other. The flow ports to be controlled open onto these two surfaces. The valve slide is an assembly of three members in overlying relation like a sandwich, the outer members or layers being of low-friction plastic material such as "Teflon," the inner or center member being of resilient compressible material (e.g., urethane, or silicone rubber) dimensioned to be under compression when the valve slide is in its channel, so that the resilience of the central layer of the slide serves to keep the outer layers constantly pressed firmly against the body surfaces on which they slide. Ports are formed in the slide assembly. If one port is to be connected to another port, this is done by means of a channel on the inner face of one of the outer members of the slide assembly, so the material flowing through the channel does not come in contact with the valve body. To mount the valve body firmly, a metal nut is provided in the plastic body, held therein by an O-ring seated in an external circumferential groove around the nut and an internal circumferential groove around the recess in which the nut is placed, in the plastic body.

7 Claims, 7 Drawing Figures

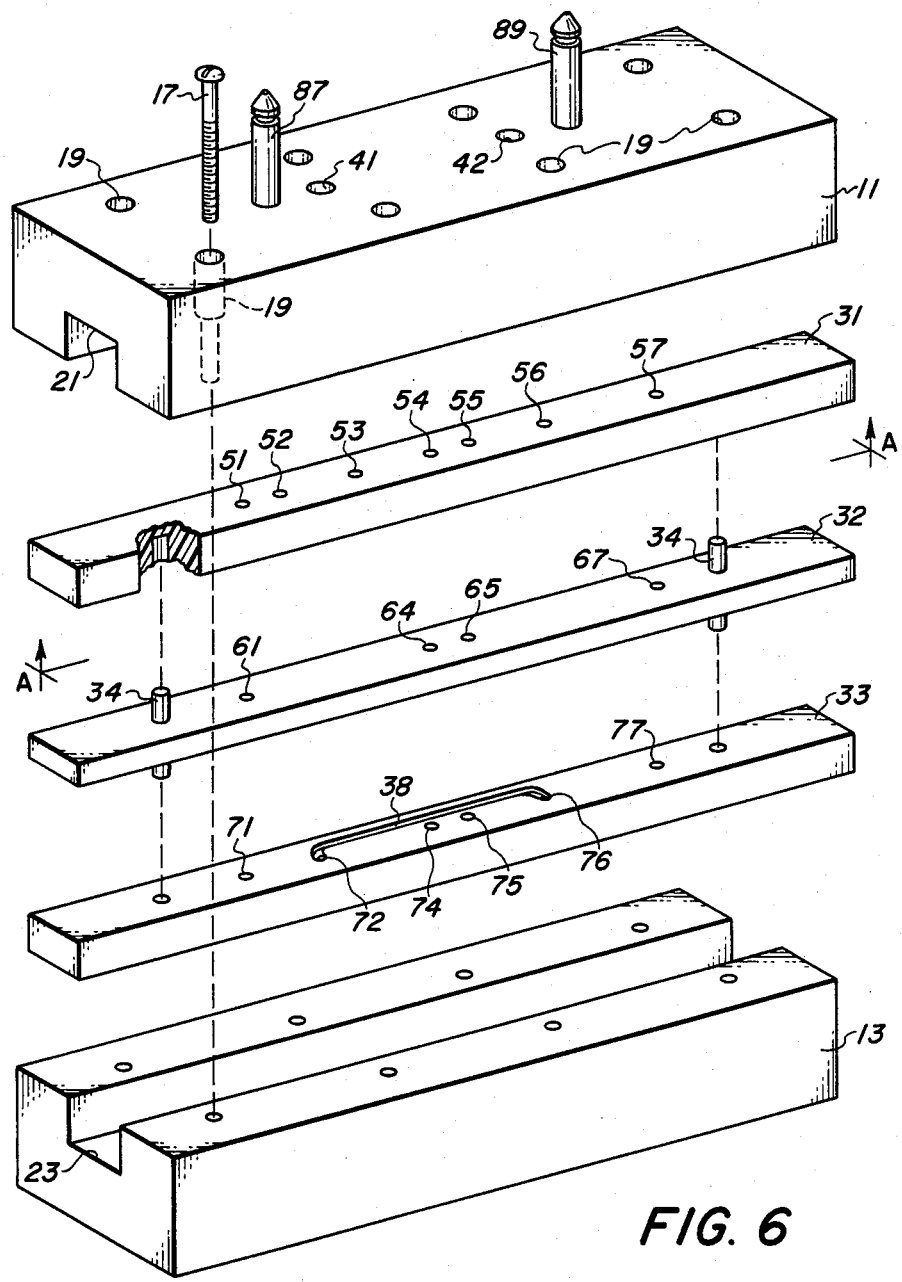

SLIDE VALVE FOR CONTROLLING FLUID FLOW

BACKGROUND OF THE INVENTION

This invention relates to a slide valve for accurately controlling the flow of fluid. Such valves are used in a variety of fields. The valve of the present invention as here disclosed has been designed especially for use in scientific or medical apparatus, such as blood testing apparatus, but the inventive features are applicable to fluid controlling slide valves in general wherever high accuracy, long life, and high resistance to corrosion from the fluids passing through the valve are desired. The word fluids is used here in its generic scientific sense, meaning both liquids and gases.

In the prior art, slide valves of the high precision and high quality type, such as used in scientific and medical apparatus, have customarily had cylindrical slides made of a solid cylinder or rod of metal. There is no way to keep such a slide constantly tight in the cylindrical chamber in which it slides. Leagage of fluid can and frequently does occur, both longitudinally from one port to another port, and also circumferentially around the periphery of the slide, in the tiny space between the slide and the surrounding body, which space gradually becomes bigger and bigger as wear continues. Thus a large part of the surface of the slide, and of the interior surface of the body surrounding the slide, becomes subject to contamination by and possible corrosive action from one or more of the fluids passing through the ports of the valve.

Moreover, the condition is made worse in those situations where the function to be performed by the valve requires that one port at one longitudinal location in the valve slide be connected with another port at a different longitudinal location in the valve slide, or perhaps at a different lateral location. In the conventional construction, any connecting channel for connecting two ports of the slide to each other is formed on the outer surface of the slide, and any fluid passing along this connecting channel necessarily comes into contact with the adjacent wall of the valve body, providing additional opportunity for corrosion in this area of the body, quite aside from the corrosion resulting from leakage which can not be eliminated as a cylindrical valve slide wears.

SUMMARY OF THE INVENTION

The present invention eliminates the above mentioned difficulties and disadvantages of the prior art, by providing a valve slide of square or rectangular cross section fitting tightly in a channel of corresponding cross section in the valve body. The valve slide is made of three strips put together in overlying relation to each other, like a sandwich. The top and bottom strips or layers are of low friction material immune to or at least highly resistant to contamination and corrosion by the fluids with which the valve is to be used. The center strip or layer, between the top and bottom strips, is of compressible resilient material, exerting constant pressure to keep the top and bottom layers pressed firmly against the ported surfaces of the valve body, on which the strips slide. Thus the cooperating ported surfaces of the valve body and the valve slide are constantly in tight engagement with each other, by reason of the resilience of the center layer of the slide, and leakage is non-existent or minimized.

If the function to be performed by the valve requires a port at one location on the slide to be connected to a port at a different location on the slide, this is done by providing a connecting channel between the two ports, the channel being formed on the inner face of the top or bottom strip making up the slide; that is, the face which is toward the compressible center layer. Thus the connecting channel is entirely within the valve slide, not on an outer face thereof, and it does not increase the area of contact of the fluid with the surface of the valve body.

This improved construction as summarized above fulfills an important object of the invention, namely, the provision of a slide valve of high accuracy and precise control, of long life, comparatively easy and inexpensive to manufacture, practically free of leakage even after long continued use, and having improved resistance to contamination and corrosion when used with fluids that may be contaminating and corrosive to a serious extent in slide valves of the prior art. This improved valve, as already indicated, finds its greatest usefulness, though not necessarily its only usefulness, in locations requiring a high quality and high precision valve, such as in scientific and medical apparatus.

Another object of the invention is to provide improved means for mounting a valve of this kind on the bed plate or other appropriate part of the apparatus with which the valve is used, as for example a blood analyzing or testing machine. The valve body should be mounted very firmly and rigidly on the base plate or other suitable part of the associated machine, and a convenient way to do this is by screws coming up through the base plate from below, and screwed into the valve body resting on top of the base plate. However, if the valve body is made of acetal plastic material such as poly vinyl chloride (PVC), as is preferably the case, it is likely that screw threads formed directly in the plastic material may not be strong enough to hold the valve body with the desired force.

Therefore, a feature of the present invention is the provision of a satisfactory and inexpensive way of mounting metal nuts in recesses in the plastic body of the valve, so that the screws coming up through the base plate may screw into these metal nuts and anchor the valve body with sufficient force. To accomplish this, the bottom face of the valve body is provided with recesses for receiving the metal nuts, and each nut is locked in its recess by an O-ring, as further explained below.

BRIEF DESCRIPTION OF THE DRAWINGS

FIG. 6 is an exploded isometric view thereof; and

FIG. 7 is a bottom view of the top strip member of the valve slide, looking in the direction of the arrows A—A of FIG. 6.

DESCRIPTION OF THE PREFERRED EMBODIMENT

Figure 1:
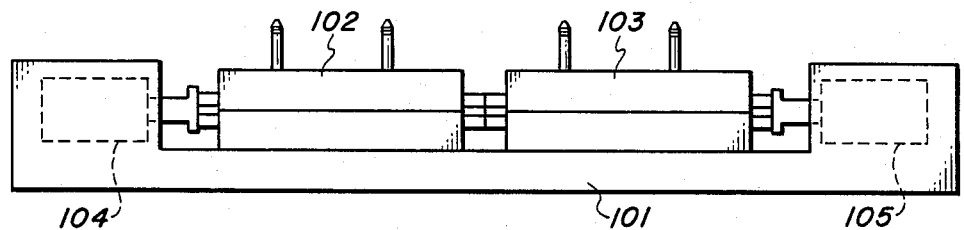
FIG. 1 is a schematic side elevation illustrating a base plate or mounting plate having thereon two slide valves according to the present invention, mounted in tandem with respect to each other, and schematically illustrating also the operating cylinders for operating the valves.

Referring now to the drawings, the body of the valve, in the preferred form, is made in two sections, an upper or top section 11 and a lower or bottom section 13 tightly fixed to each other by any desired number of screws 17 the heads of which are recessed in counterbores 19 in the upper member while the shanks of the screws extend into tapped bores in the lower member 13, as will be best understood from FIG. 6. For a valve body having a length of about 4½ inches, eight screws are preferred and are here shown. A shorter valve body about 3¼ inches long would ordinarily have six screws.

Both parts of the valve body are made of the same material, preferably an acetal plastic material which is relatively hard and rigid, and highly resistant to corrosion by the fluids which are to flow through and be controlled by the valve. Polyvinyl chloride (PVC) is satisfactory for this purpose, when the fluids in question are blood and the usual reagents customarily used in blood analyzing or testing apparatus.

Figure 5:
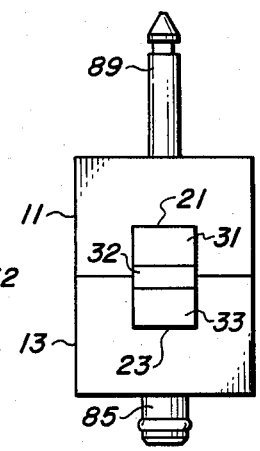
FIG. 5 is a right hand end view thereof.

The bottom face of the upper body section 11 and the top face of the lower body section 13 are provided with longitudinal rectangular channels which mate with each other to form one large channel when the two body sections are assembled against each other in the normal manner, as readily apparent from FIGS. 5 and 6. The bottom surface of the channel in the member 11 is designated at 21, and the bottom surface of the channel in the member 13 is designated at 23.

The channel is of uniform cross sectional dimensions throughout its length. Slidable longitudinally in this channel is the slide member made up of three layers 31, 32, and 33. They are placed in overlying relation to each other, like a sandwich, as will be plainly seen from the exploded view, FIG. 6, and from the end view, FIG. 5. Locating pins 34 passing snugly through the intermediate layer 32 and extending snugly part way through the thicknesses of the top and bottom layers 31 and 33 serve to prevent any longitudinal slippage of one member or layer relative to another, and to insure that all three members 31, 32, and 33 will move together as a unit.

The top and bottom layers 31 and 33 of the slide are made preferably of the plastic material identified by the trademark "Teflon," which is widely known under this name and is available on the market. This material is excellent for purposes of the present invention, as it is a low friction material, that is, it has a comparatively low coefficient of sliding friction when sliding on the material of which the body parts 11 and 13 are made, and in addition, the Teflon has a high resistance to corrosion by many fluids, including the specific fluids above mentioned, and high resistance to contamination in that it does not readily absorb the fluids likely to flow through the valve.

The middle strip 32 of the slide is, as above stated, compressible and resilient, and is of such thickness that it is somewhat compressed when the slide member is in its channel in the valve body. Thus this member 32 exerts constant force upwardly on the member 31 and downwardly on the member 33, keeping the upper surface of the upper slide member 31 always tight against the bottom surface 21 of the groove or channel in the upper body member 11 and keeping the bottom surface of the lower slide member 33 always tight against the bottom surface 23 of its groove or channel in the lower body member 13. Urethane is a satisfactory material from which to form the resilient or elastic strip 32. Also silicone rubber is a satisfactory material. The silicone rubber is relatively temperature stable, and is inert with respect to the fluids flowing through the valve when the valve is used in blood analyzing apparatus.

The number of fluid flow ports and the location of ports, both in the valve body and in the slide, are matters of choice depending upon the flow conditions which are to be controlled by the valve, and the details of the number and location are not important so far as the present invention is concerned. Merely as a typical example, the valve shown in the drawings as an illustrative embodiment has two ports 41 and 42 in the upper body section 11, these ports opening at the surface 21 of the slide-receiving channel. The illustrative example also has seven ports extending vertically through the thickness of the upper slide member 31, these seven ports being shown in FIG. 6 and being numbered consecutively from left to right as 51 through 57.

The resilient compressible central strip 32 of the slide has four ports, designated in FIG. 6 as 61, 64, 65, and 67, which are aligned with the ports 51, 54, 55, and 57, respectively.

The lower strip 33 of the valve slide has six ports 71, 72, 74, 75, 76, and 77. Of these, the port 71 is aligned with the ports 61 and 51; the port 74 is aligned with ports 64 and 54; the port 75 is aligned with ports 65 and 55; and the port 77 is aligned with ports 67 and 57. The port 72 is not aligned with any other port. The port 76 happens to be in line with the port 56, but is not connected to it because the intervening layer 32 is imperforate at this point.

Figure 3:
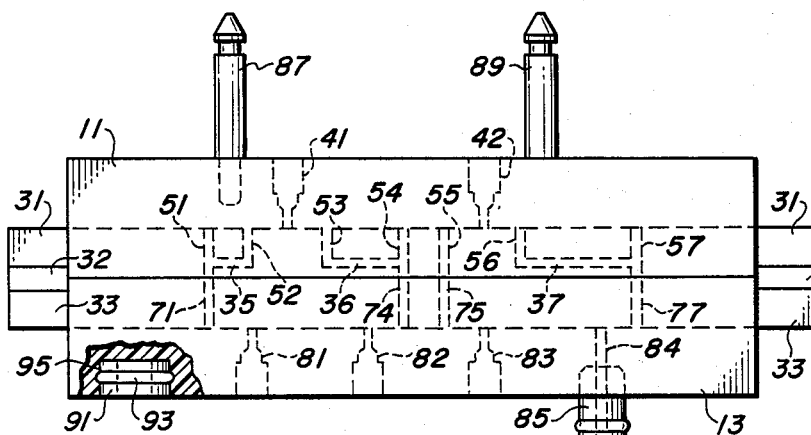
FIG. 3 is a front elevational view of the same, with parts broken away and certain interior parts illustrated in dotted lines.
Figure 4:
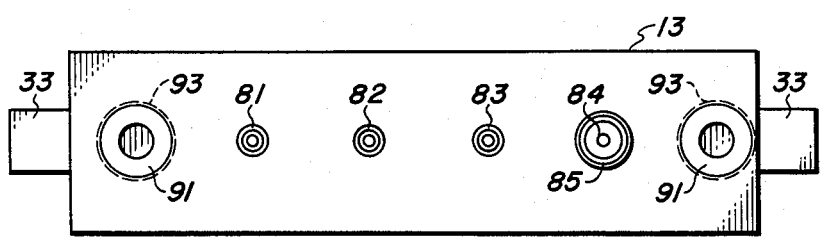
FIG. 4 is a bottom plan view thereof.

The bottom section 13 of the valve body has four ports, designated in FIGS. 3 and 4 as 81, 82, 83, and 84. The port 84 is provided with a fitting 85 surrounded by an O-ring, for connection to a conventional fitting of a conventional air pressure supply hose. The other ports 81, 82, and 83 have counterbored enlargements at their outer ends, into which conventional fluid conduits may be inserted with a tight frictional fit, or any other conventional means of attaching fluid conduits may be employed.

Although the number of the valve ports and the spacing of the ports are immaterial so far as the present invention is concerned, yet it is a feature of the present invention to connect different ports to each other by channels which are formed on interior surfaces of the valve slide, rather than on exterior surfaces thereof. If the function to be performed by the valve requires that, for example, the port 51 be connected to the port 52, this is done by cutting a channel 35 (FIG. 7) in the under face of the strip 31, between the ports 51 and 52. Such a channel is easily and inexpensively formed in the surface of the strip during the manufacturing process, and then when the layers of the slide member are assembled, the middle layer 32 will serve to close or seal the open side of the channel. Similarly, a channel 36 formed in the same lower face of the strip 31 serves to connect the ports 53 and 54, and another channel 37 formed in the same face of the strip serves to connect the ports 56 and 57 with each other.

FIG. 6 illustrates a channel 38 formed in the upper face of the bottom strip 33 of the slide, connecting the ports 72 and 76 which each other. This channel is offset to one side of the intervening ports 74 and 75 and does not connect with them. As in the case of the channels previously mentioned, when the parts are assembled, the adjacent face of the intermediate strip 32 serves to close and seal the open side of the channel 38.

Figure 2:
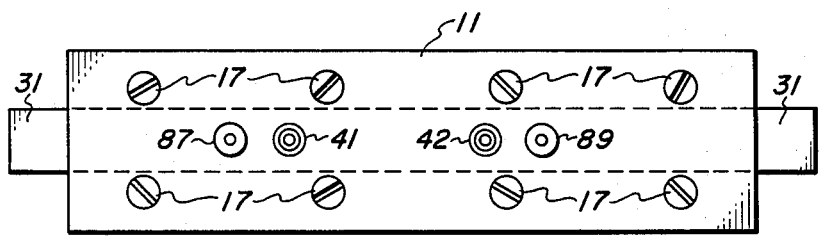
FIG. 2 is a top plan view of a slide valve according to a preferred embodiment of the invention.

Some but not all of the ports and channels are illustrated in dotted lines in FIG. 3. This view, as well as FIGS. 2 and 4, show the valve slide in its intermediate or no-flow position. Merely for the purpose of describing a typical illustrative cycle of operation of the valve, let it be assumed that a liquid cassette of conventional known construction is mounted on top of the valve by means of the conventional locating posts or pins 87 and 89 and such other conventional mounting means as may be desired, and that the inlet and outlet conduit connections of the cassette are properly inserted into the sockets at the tops of the ports 41 and 42 in the upper section of the valve body. Also let it be assumed that a conventional compressed air supply is connected to the fitting 85 of the bottom portion of the valve body, and that the sockets at the bottoms of the ports 81, 82, and 83 are suitably connected to conventional conduits leading to conventional fluid containers.

Now if the valve slide is moved a short distance to the left from the central position shown in FIG. 3, so that the port 77 of the slide lines up with the port 84 of the body, compressed air may enter through the port 84, and through the aligned ports 77, 67, and 57, thence through the channel 37 to the port 56, which will now be aligned with the port 42, so compressed air will enter the cassette mounted on the valve, tending to expel any liquid that is in the cassette. The port 53 will now be aligned with the port 41, so that the liquid in the cassette will be driven out through the second connection of the cassette to the port 41, thence into and through the port 53, channel 36, and ports 54, 64, and 74, exiting through the body port 82 which is now aligned with the slide port 74.

If the valve slide is moved a corresponding distance to the right from the central position shown in FIG. 3, then no port of the slide will line up with the compressed air port 84 of the body, but the port 71 of the slide will line up with the body port 81, and the slide port 75 will line up with the body port 83. Also, slide ports 52 and 55 will be alined with body ports 41 and 42, respectively. So one connection of the cassette on the valve body will communicate through ports 41 and 52, channel 35, and ports 51, 61, and 71, with port 81 and whatever external conduit is connected to it, while the other connection of the cassette will communicate through ports 42, 55, 65, 75, and 83 with whatever external conduit is connected to the port 83.

As above mentioned, this is merely a typical example. The porting of the valve body and of the slide may be varied widely without departing from the invention.

In a typical use of the valve, two or more of such valves may be mounted in tandem on a base plate or mounting plate such as shown schematically at 101 in FIG. 1. A first valve is shown at 102, and a second valve at 103, the slides of the two valves being in end-to-end contact with each other, so that one pushes the other. To push the slides, fluid cylinders 104 and 105 are mounted at opposite ends, these cylinders being either pneumatic or hydraulic, with piston rods engaging the respective ends of the valve slides. When cylinder 104 is pressureized and the pressure in cylinder 105 is relieved, the slides of both valves 102 and 103 will be moved to their right hand positions, and vice versa when cylinder 105 is pressurized and cylinder 104 is relieved. This position of mounting valves is conventional and is here shown only to illustrate a typical manner of using the valve of the present invention.

Such valves are customarily held down on the bed plate or base plate by screws coming up from beneath, through the plate. These screws, if simply screwed into threads formed in the plastic material of which the valve body is formed, may not hold the valve body sufficiently well, because when plastic material of this kind is under stress or tension, such as the pressure exerted on the plastic screw threads, it has a tendency to break down or disintegrate under the influence of corrosive materials which the plastic may be able to withstand adequately when not under stress or tension. Therefore, a feature of the invention is to provide the plastic valve body with metal nuts for receiving the mounting screws, and to provide an improved way of holding the nuts in the body, in such manner that the plastic body is not subjected to undesirable stress.

In the lower face of the valve body 13, near each end thereof, a recess is formed for receiving a metal nut which is internally threaded to receive a retaining screw. The nut is externally circular in shape, rather than having a hexagonal or other polygonal external shape as conventional in most nuts. These nuts, shown at 91 in FIGS. 3 and 4, are provided around their peripheries, about midway of the length of the nut, with a circumferential groove in which an elastic O-ring 93 of rubber or the like is seated. The plastic body 13 of the valve is provided at each desired nut location with a recess 95 of a size th receive the nut rather snugly, and this recess has an internal circumferential groove to receive the O-ring.

The nut with the O-ring seated thereon is thrust forcibly into its recess. Considerable force is required to compress the resilient O-ring sufficiently to pass into the recess, but when sufficient force is exerted, the nut and O-ring can be forced into the recess. Once seated in the recess, the O-ring expands into the internal groove in the recess, and thereafter it is practically impossible to pull the nut out of the recess. It is an inexpensive and comparatively easy way of mounting the metal nut in the plastic body, and it provides an excellent strong anchorage for anchoring the valve body on the mounting plate of the apparatus by means of screws coming up through the plate.

It should be noted that the bottom face of the nut 91 is flush with the bottom surface of the body section 13. Therefore, when the valve is mounted on the usual flat mounting plate, the plastic body of the valve will not be unduly stressed or tensioned no matter how firmly the screws are tightened. The force of a screw on a nut simply seats the nut firmly against the base plate, and is not transmitted through the plastic material. The O-ring on the nut provides gentle pressure on the plastic material to hold the plastic body against the mounting plate, but this pressure is independent of the degree of force exerted by the screw in the nut.

What is claimed is:

1. A slide valve for controlling fluid flow, comprising a body having two surfaces spaced from and parallel to each other, each of said surfaces having at least one port opening in such surface, a slide assembly slidable longitudinally in the space between said two parallel surfaces, said slide assembly being formed of at least two members overlying each other, one member of the assembly sliding along and being tightly engaged with one of said two parallel surfaces, another member of the assembly sliding along and being tightly engaged with the other of said two parallel surfaces, one member of the slide assembly being resilient and being compressed in a direction perpendicular to said two parallel surfaces so that the resilience thereof tends to hold the slide assembly tightly engaged with said two parallel surfaces of said body, and porting means in said members of said slide assembly for forming a connecting passage from a port in one of said surfaces to a port in the other of said surfaces when said slide assembly is in a predetermined longitudinal position in said body, said porting means including at least two ports extending through the thickness of one member of the slide assembly, and a channel forming a passageway between one of said ports and another of said ports, said channel being formed along an inner surface of said one member and out of contact with said body.

2. A slide valve for controlling fluid flow, comprising a body having two surfaces spaced from and parallel to each other, each of said surfaces having at least one port opening in such surface, a slide assembly slidable longitudinally in the space between said two parallel surfaces, said slide assembly being formed of three members in overlying relation to each other, one outer member of the assembly sliding along and being tightly engaged with one of said two parallel surfaces, the other outer member of the assembly sliding along and being tightly engaged with the other of said two parallel surfaces, the middle member of the slide assembly being resilient and being compressed in a direction perpendicular to said two parallel surfaces so that the resilience thereof keeps the outer members of the slide assembly tightly engaged with said two parallel surfaces of said body, and porting means in said members of said slide assembly for forming a connecting passage from a port in one of said surfaces to a port in the other of said surfaces when said slide assembly is in a predetermined longitudinal position in said body, said porting means including a plurality of ports extending through the thickness of one of said outer members, and a channel forming a passageway between two of such ports, said channel being formed in the surface of an outer member which is adjacent to said middle member.

3. The invention defined in claim 2, wherein said outer members are of low friction plastic material.

4. The invention defined in claim 3, wherein said outer members are of "Teflon."

5. The invention defined in claim 2, wherein said middle member is of urethane.

6. The invention defined in claim 2, wherein said middle member is of silicone rubber.

7. A slide valve for controlling fluid flow, comprising a body having two surfaces spaced from and parallel to each other, each of said surfaces having at least one port opening in such surface, a slide assembly slidable longitudinally in the space between said two parallel surfaces, said slide assembly being formed of at least two members overlying each other, one member of the assembly sliding along and being tightly engaged with one of said two parallel surfaces, another member of the assembly sliding along and being tightly engaged with the other of said two parallel surfaces, one member of the slide assembly being resilient and being compressed in a direction perpendicular to said two parallel surfaces so that the resilience thereof tends to hold the slide assembly tightly engaged with said two parallel surfaces of said body, and porting means in said members of said slide assembly for forming a connecting passage from a port in one of said surfaces to a port in the other of said surfaces when said slide assembly is in a predetermined longitudinal position in said body, said valve body being of plastic material and having a recess therein with an internal groove extending circumferentially around the recess at a location spaced inwardly from the outer end of the recess, further comprising a metallic nut internally screw threaded and mounted snugly in said recess, said nut having an external groove extending circumferentially around the periphery of the nut, and a resilient O-ring surrounding said nut and seated in the external groove of the nut and the internal groove of the recess to retain the nut against removal from the recess, whereby the screw threads of the nut may receive a screw exerting sufficient force to mount said valve body firmly on a support.

* * * * *